(12) United States Patent
Chinn et al.

(10) Patent No.: US 7,548,788 B2
(45) Date of Patent: Jun. 16, 2009

(54) OPERATING ROOM LEAD CONNECTOR

(75) Inventors: Kenny Kinyen Chinn, Castaic, CA (US); Carla Mann Woods, Beverly Hills, CA (US); Stephen L Goldman, Frisco, TX (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 593 days.

(21) Appl. No.: 11/192,257

(22) Filed: Jul. 28, 2005
(Under 37 CFR 1.47)

(65) Prior Publication Data

US 2006/0030918 A1 Feb. 9, 2006

Related U.S. Application Data

(60) Provisional application No. 60/598,813, filed on Aug. 4, 2004.

(51) Int. Cl.
| | |
|---|---|
| *A61N 1/02* | (2006.01) |
| *A61N 1/00* | (2006.01) |
| *A61N 1/372* | (2006.01) |
| *A61N 1/375* | (2006.01) |

(52) U.S. Cl. .......................................... 607/117; 607/37
(58) Field of Classification Search .................... 607/37, 607/117
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 3,822,708 A | 7/1974 | Zilber | |
| 4,338,945 A | 7/1982 | Kosugi et al. | |
| 4,379,462 A | 4/1983 | Borkan et al. | |
| 4,614,395 A | 9/1986 | Peers-Trevarton | |
| 5,121,754 A | 6/1992 | Mullett | |
| 5,261,395 A | 11/1993 | Oleen et al. | |
| 5,354,326 A | 10/1994 | Comben et al. | |
| 5,366,494 A * | 11/1994 | Holleman et al. | 607/119 |
| 5,417,719 A | 5/1995 | Hull et al. | |
| 5,501,703 A | 3/1996 | Holsheimer et al. | |
| 5,931,861 A * | 8/1999 | Werner et al. | 607/115 |
| 6,038,479 A * | 3/2000 | Werner et al. | 607/115 |
| 6,038,481 A * | 3/2000 | Werner et al. | 607/119 |
| 6,192,278 B1 * | 2/2001 | Werner et al. | 607/115 |
| 6,321,126 B1 | 11/2001 | Kuzma | |
| 6,343,233 B1 * | 1/2002 | Werner et al. | 607/119 |
| 6,516,227 B1 | 2/2003 | Meadows et al. | |
| 6,687,538 B1 | 2/2004 | Hrdlicka et al. | |
| 6,895,280 B2 | 5/2005 | Meadows et al. | |
| 2002/0143376 A1 * | 10/2002 | Chinn et al. | 607/115 |
| 2004/0093051 A1 * | 5/2004 | Chinn et al. | 607/116 |

* cited by examiner

*Primary Examiner*—Carl H Layno
*Assistant Examiner*—Yun Haeng Lee
(74) *Attorney, Agent, or Firm*—Darby & Darby P.C.; Patrick R. Turner

(57) ABSTRACT

An operating room connector is used in conjunction with a multiple electrode SCS system which can easily detach and connect to an external trial stimulator (ETS). By connecting the electrode SCS system to a stylet handle, and then locking the stylet handle within a slot of the connector platform, a user is able to minimize the required steps in connecting the ETS to the implanted SCS lead system. The ETS can then be used to readjust the position of the electrode array(s) previously implanted to deliver an optimal stimulation therapy.

20 Claims, 10 Drawing Sheets

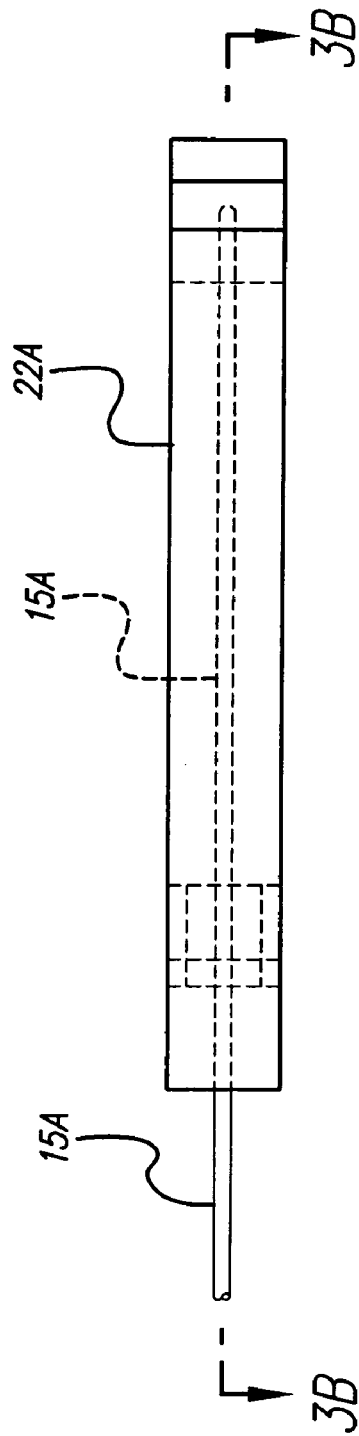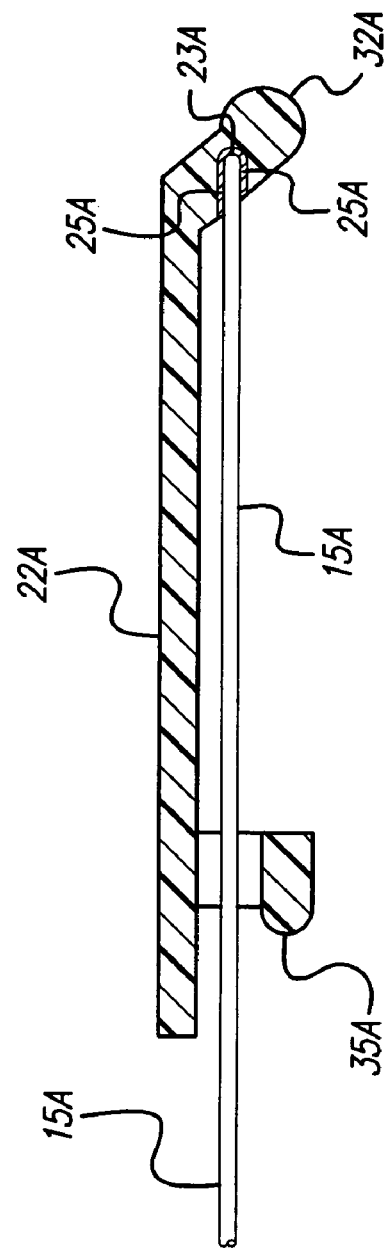

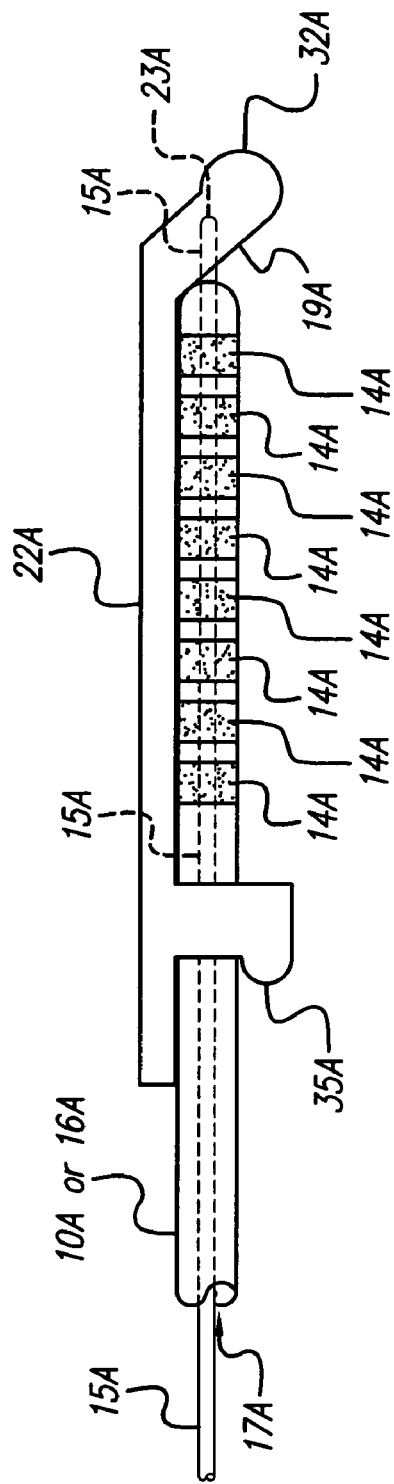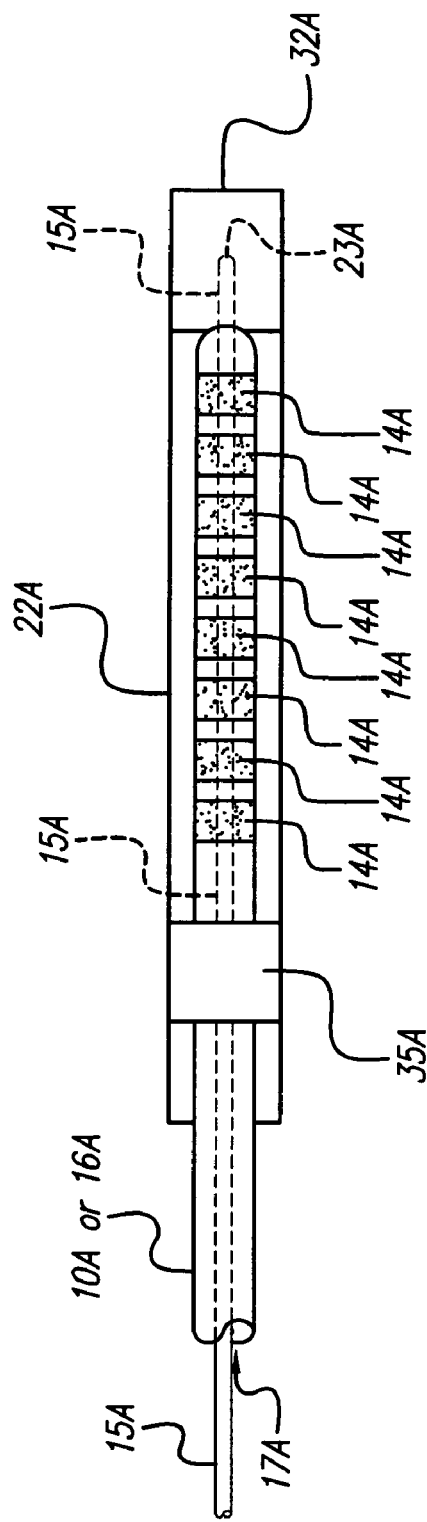

OPERATING ROOM LEAD CONNECTOR

The present application claims the benefit of U.S. Provisional Patent Application Ser. No. 60/598,813, filed 4 Aug. 2004, which application is incorporated herein by reference in its entirety.

FIELD OF THE INVENTION

The present invention relates to medical lead systems and, more particularly, to a connector system used with medical stimulating leads and external trial stimulators.

BACKGROUND OF THE INVENTION

The term "lead" will be used herein to describe a plurality of elongate conductors covered by insulation. At a distal end of the lead, each conductor is connected to an exposed (non-insulated) electrode, or electrode contact, which is adapted to provide an electrical interface with the tissue that is to be stimulated. At a proximal end of the lead, each conductor is connected to an exposed terminal, which terminal is adapted to provide an electrical interface with a pulse generator, or with a connector of an extension lead that connects with a pulse generator. The pulse generator may be an implantable pulse generator (IPG) or an external trial stimulator (ETS), as explained hereinafter. The term "electrode array" will refer to that portion of the lead having a plurality of spaced-apart electrode contacts. The terms "electrode" and "electrode array" will be used herein interchangeably. At the proximal end of the lead, a plurality of electrical contacts, or terminals, can be connected directly to an implantable pulse generator (IPG), or as required depending upon the location where the IPG is implanted, to an electrical connector of one or more lead extensions, which lead extension(s) can be connected to the IPG. The electrode contacts on the distal end of the lead interface with tissue and can deliver a current from the IPG which causes the tissue to be stimulated. In the instance where an external trial stimulator (ETS) is required, the lead extension(s) can be connected to another type of electrical connector, referred to as an operating room (OR) connector, or trial connector, which OR or trial connector is part of or connected to an operating room (OR) cable. The OR cable can then be connected to an ETS, or similar medical equipment. The electrode contacts on the distal end of the lead interface with tissue and can deliver a current from the ETS which cause the tissue to be stimulated.

A clinical method that is well accepted in the medical field for reducing pain in certain populations of patients is known as Spinal Cord Stimulation (SCS). An SCS system typically includes an implanted pulse generator and leads, which leads are comprised of lead wires, and electrode contacts that are connected thereto. The pulse generator generates electrical pulses that are delivered to the dorsal column within the spinal cord through the electrode contacts which are implanted along the dura of the spinal cord. In a typical situation, the attached leads exit the spinal cord and are tunneled around the torso of the patient to a subcutaneous pocket where the pulse generator is implanted. Representative spinal cord stimulation systems are disclosed in the following patents: U.S. Pat. Nos. 3,646,940; 3,724,467; 3,822,708; 4,338,945; 4,379,462; 5,121,754; 5,417,719; 5,501,703; 6,516,227; and 6,895,280, which patents are incorporated herein by reference.

Electrode arrays currently used with known SCS systems may employ between one and sixteen electrode contacts on a distal end of a lead or leads. Electrode contacts are selectively programmed to act as anodes, cathodes, or disconnected (turned off), creating an electrode configuration. The number of electrode configurations available, combined with the ability of pulse-generating circuits to generate a variety of complex stimulation pulses, presents a huge selection of stimulation parameter sets to the clinician. When an SCS system is implanted, a "fitting" procedure is performed to select an effective stimulation parameter set for a particular patient. Such a session of applying various stimulation parameters and electrode configurations may be referred to as a "fitting" or "programming" session. Additionally, a series of electrode configurations to be applied to a patient may be organized in a steering programmable table or in another suitable manner.

In order to achieve an effective result from spinal cord stimulation, the lead or leads may be placed in a location such that the electrical stimulation will create a stimulation felt by the patient known as paresthesia. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy.

In order to test the effectiveness on a particular patient of various stimulation parameters and electrode configurations, it is often necessary to connect the lead or leads to an ETS to optimize the position of the electrode array along the dura of the spinal cord. During this intra-operative procedure, the proximal end of the lead or lead extension needs to easily connect to an intermediate operating room (OR) cable and thereafter to an ETS.

An ETS is an external device that replicates some or all of the IPG's functions and is used to evaluate the efficacy of the proposed therapy. An ETS typically includes a diagnostics module used to provide valuable feedback to the user (physician, clinician, or patient). The user can then determine whether the implanted lead is operational in delivering stimulation therapy, is reliable, and comfortable. The user then concludes if readjusting the position of the implanted lead will be necessary. The ETS is externally worn for a period of typically seven to ten days for evaluation purposes before implantation of the IPG. The ETS is typically applied with an adhesive patch to the skin of the patient, but may also be carried by the patient through the use of a belt clip or other form of convenient carrying pouch. Features of the ETS may also include: (a) usability in the operating room (OR) to test the electrode array during placement, (b) a full bi-bidirectional communication capability with the clinician's programming (CP) system, and (c) the ability to allow the patient or clinician to evaluate the stimulus levels.

In the past, the known technology has allowed only one type of single electrode lead to be connected to the OR cable at a single time. If multiple electrode arrays were to be implanted, the technology would only allow one electrode array to be tested at a single time. One obvious solution would require two OR cables and two trial stimulators. The required additional equipment for testing a multiple electrode array stimulation system would add complexity and time to the surgery. Current lead OR connectors also require alignment procedures or multiple assembly steps before the connection is complete, which also adds additional complexity and time to the "fitting" and or "programming" sessions.

As the electronic medical devices implanted in patients have become more sophisticated in providing a wider range of stimulation therapies which require multiple electrode arrays, there has arisen a critical need for a reliable, easy-tomanufacture OR connector that allows the multiple electrode array system to be detachably and reliably connected to an external trial stimulator.

It is thus evident that improvements are still needed in OR connector systems, particularly to facilitate connecting an external trial stimulator with a multiple electrode array system.

SUMMARY OF THE INVENTION

The teachings of the present disclosure address the above and other needs by providing a stimulation system and method that permits detachably connecting multiple implantable leads to an external trial stimulator to optimize the position of the electrode array along the spinal cord.

That is, in one aspect, the present disclosure provides an embodiment of a connector system that provides of multiple rows of mating contacts that can electrically connect one or more implantable leads for simultaneous stimulation with an external trial stimulator. The multiple rows of mating contacts are enclosed within open slots on a flat surface of a connector platform.

In accordance with the teachings of the present disclosure, at least two open slots or attachment areas are made available on a flat surface of a connector platform for purposes of detachably connecting a dual electrode lead assembly. Three or more open slots are also possible, wherein the additional open slots would allow the user the flexibility to have several connecting open slots available during the connection process of an external trial stimulator or other similar medical equipment.

In accordance with the teachings of the present disclosure, the connecting open slots are substantially parallel to each other and extend along a surface of the connector platform. Spaced apart mating contacts are provided in each slot. A stylet wire which is permanently attached to a stylet handle engages a lead or lead extension through a central lumen. The stylet handle acts as a quick connect interface that positively locates and clips down onto any of the available parallel open slots of the connector platform. The stylet handle also acts as a carrier which secures the plurality of spaced-apart electrical terminals, located at the proximal end of the lead within the open slot. The corresponding mating contacts along the open slot align with the plurality of spaced-apart electrical terminals, thereby allowing an electrical connection to be made between the contacts and terminals.

In accordance with yet another feature of the invention, a stylet handle is used to house and protect the proximal electrical terminals of the lead or lead extension. The stylet handle acts as a quick connect interface that individually locates an implantable lead onto a connector platform.

Another embodiment of the present invention is a method for positioning a multiple lead assembly along the dura space of a patient or other suitable location. The multiple leads include a distal end and a proximal end. The distal end has a plurality of spaced-apart electrode contacts and the proximal end has a plurality of spaced-apart electrical terminals. Wires carried within the body of each lead connect respective terminals to respective electrode contacts. Each lead is engaged with a stylet wire having a stylet handle, which stylet wire may be permanently attached to the stylet handle. The stylet wire is threaded through a central lumen that runs the entire length of each lead. The stylet handle interfaces with a connector platform which positively engages the plurality of electrical terminals of each lead with corresponding mating contacts within an open slot or attachment area of the connector platform. An OR cable is used to connect the connector platform and the external trial stimulator. The distal end of the lead may be repositioned as needed with the stylet wire until enough data has been gathered from the external trial stimulator to indicate that an optimal position for the electrode array has been established. Once an optimal position is established, the stylet handle is disconnected from the connector platform and the stylet wire is removed from the lead system. The lead system is then finally connected to an IPG. The IPG is thereafter used for applying current stimulation pulses to the implanted electrode array, thereby allowing an effective stimulation therapy to thereafter commence through the use of the IPG.

BRIEF DESCRIPTION OF THE DRAWINGS

The above and other aspects, features and advantages of the present invention will be more apparent from the following more particular description thereof, presented in conjunction with the following drawings wherein:

FIG. 3A shows a top view of a preferred embodiment of a stylet handle of the present invention;

FIG. 3B is a cross sectional view of the stylet handle shown in FIG. 3A taken along line 3B-3B;

FIG. 4B is a side view of the stylet handle and stylet wire shown in FIG. 3A with the lead or lead extension positioned within the stylet handle;

FIG. 4C is a bottom view of the stylet handle and stylet wire shown in FIG. 3A with the lead or lead extension positioned within the stylet handle;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
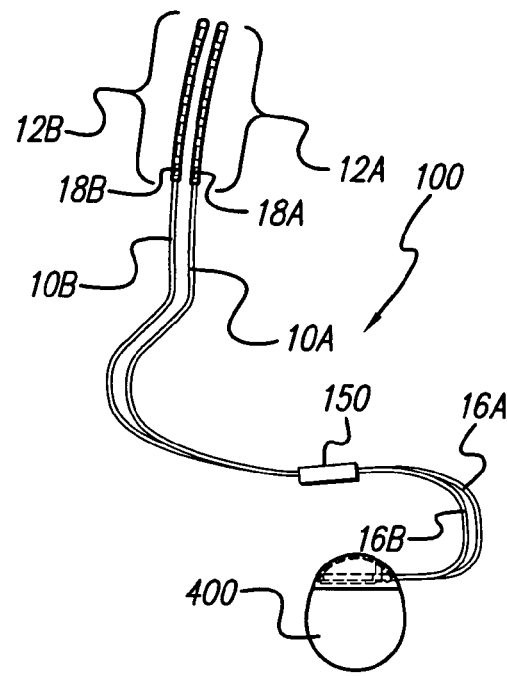
FIG. 1A shows a Spinal Cord Stimulation (SCS) system having an exemplary dual electrode system.

For illustration purposes, the following description is provided in conjunction with a Spinal Cord Stimulation (SCS) system. Other types of stimulation systems may also be used such as, but not limited to, cochlear implants, cardiac stimulation systems, peripheral nerve stimulation systems, brain stimulation systems and microstimulators. A dual SCS lead system 100 is shown in FIG. 1A. The SCS system 100 typically comprises a rechargeable, multichannel, 16-contact (or more), telemetry-controlled pulse generator housed, for instance, in a rounded titanium hermetically sealed enclosure, known as an Implantable Pulse Generator (IPG) 400. The dual SCS lead system 100 shown in FIG. 1A also contains two lead extensions 16A and 16B, two electrode leads 10A and 10B each having an electrode array 12A and 12B at a distal end. The IPG 400 generates current stimulation pulses and delivers such stimulation pulses to the plurality of implanted electrode contacts 18A and 18B included with the electrode arrays 12A and 12B. The proximal end of each lead extension 16A and 16B is removably connected to the IPG 400. The distal end of each lead extension 16A and 16B is removably connected to a proximal end of a corresponding electrode lead 10A or 10B using a lead connector(s) 150. An electrode array 12A and 12B is formed on a distal end of each electrode lead 10A and 10B. The in-series combination of the lead extension 16A and electrode lead 10A, carry the stimulation current from the IPG 400 to the electrode array 12A, thereby providing a tingling sensation felt by the patient known as a "paresthesia". Also, the in-series combination of the lead extension 16B and electrode lead 10B, similarly carry the stimulation current from the IPG 400 to the electrode array 12B delivering the "paresthesia". Note, as used herein, the term "paresthesia" refers to that area or volume of the patient's tissue that is affected by the electrical stimuli applied through the plurality of electrode contacts 18A and 18B. The patient may typically describe the paresthesia as an area where a tingling sensation is felt.

Figure 1B:
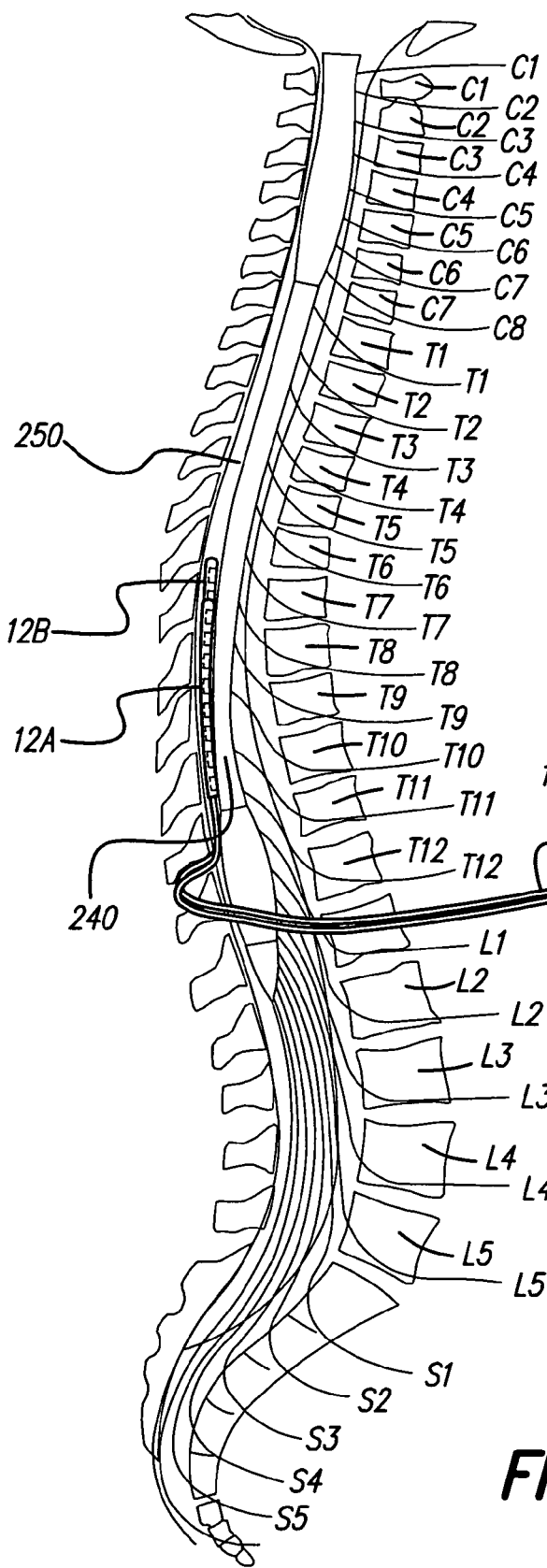
FIG. 1B depicts the SCS system of FIG. 1A implanted to stimulate tissue near a spinal column.

The SCS system 100 described in FIG. 1A, is depicted implanted in the epidural space 250 shown in FIG. 1B. The set of electrode arrays 12A and 12B are implanted at the site of nerves that are the target of stimulation, e.g., along the spinal cord 240. Due to the lack of space near the location where the electrode leads 10A and 10B exit the spinal column, the IPG 400 is generally implanted in the abdomen, above the buttocks, or other suitable location. The lead extensions 16A and 16B facilitate locating the IPG 400 away from the electrode lead exit point.

In a preferred embodiment, two or more electrode arrays 12A and 12B may be implanted in the patient. Having a relatively greater number of electrode contacts increases the area of the body that can be affected by stimulation, or the "area of potential stimulation." The area of potential stimulation corresponds roughly to the area of the body mapped to the dermatomes for the area of the spine adjacent to the implanted electrodes. The area of potential stimulation may be divided into sections, each section corresponding to the electrodes that typically provide stimulation to that section of the body.

A more detailed description of a representative SCS system that may be used with the present disclosure is described in U.S. Pat. No. 6,516,227, previously incorporated herein by reference. It is to be emphasized, however, that the disclosure herein described may be used with many different types of stimulation systems, and is not limited to use only with the representative SCS system described in the '227 patent.

An external trial stimulator (ETS) 300 (shown in FIG. 2) is used with the dual SCS lead system described above during, e.g., the first seven to ten days after implantation of the multiple lead assembly and before implantation of the hermetically sealed IPG 400. The ETS 300 is typically used to test the efficacy of the electrode system, e.g., for testing the stimulation therapy and or for fitting purposes. In this manner, the patient can provide valuable feedback as to the effectiveness of the stimulation therapy. The stimulus or position of the electrode array can change several times until a satisfactory "paresthesia" is found. After the testing period, the ETS 300 is disconnected and surgery for implanting the IPG 400 can commence. Once the IPG 400 is implanted in the abdomen, above the buttocks, or any other suitable location, the IPG 400 may be programmed to provide the patient with his or her personalized stimulation therapy previously obtained during the testing period.

For medical professionals involved with the testing period, a challenge exits for connecting a multiple lead assembly to the ETS 300. The connecting system must not only be reliable, but also must possess a multiplicity of connecting slots that can accommodate the most current SCS components available in the medical field.

Figure 2:
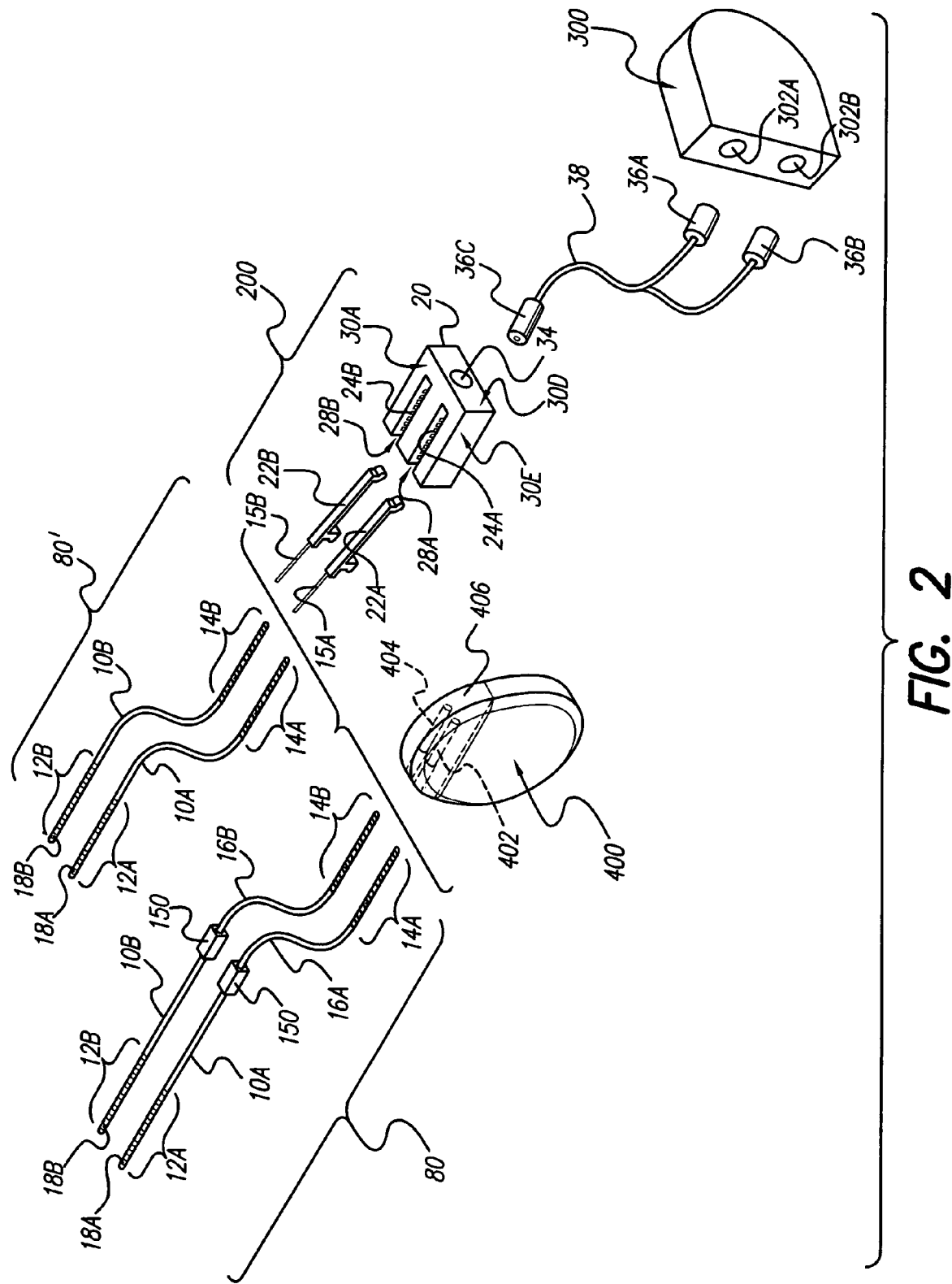
FIG. 2 shows an exploded view of the various components of the SCS system and various components of an ETS connecting system.

A connecting system 200 made in accordance with one embodiment of the invention is shown in FIG. 2. Dual lead assemblies 80 or 80' may be used with the SCS system. The dual lead assemblies 80 and 80' consist of two electrode arrays 12A and 12B located at the distal end of each lead 10A and 10B. Each electrode array 12A and 12B includes a plurality of spaced-apart electrode contacts 18A and 18B, e.g., eight electrode contacts are included within the distal end of each electrode array. The electrode contacts 18A and 18B are exposed to the tissue to be stimulated. At the proximal end of the lead assembly 80, two connectors 150 are used to connect lead extensions 16A and 16B. The lead extensions 16A and 16B contain a plurality of spaced-apart electrical terminals 14A and 14B, which terminals connect to an implantable pulse generator (IPG) 400. In contrast, the dual lead assembly 80' does not require lead extensions 16A and 16B, since electrical terminals 14A and 14B located at the proximal ends of each lead 10A and 10B may be directly connected to the IPG 400. It is to be emphasized that the dual lead assemblies 80 and 80' are only exemplary, two or more lead assemblies may be used.

The IPG 400 contains stimulating electrical circuitry ("stimulating electronics"), a power source, e.g., a rechargeable battery, and a telemetry system. Typically, the IPG 400 is placed in a surgically-made pocket either in the abdomen, or just at the top of the buttocks. It may, of course, also be implanted in other locations of the patient's body. Once implanted, the IPG 400 may be connected to the lead assembly 80 through connecting orifices 402 and 404 located in the header portion 406 of the IPG 400. The lead extensions 16A and 16B, for example, may be tunneled up to the spinal column. Once implanted, the electrode arrays 12A and 12B, leads 10A and 10B, and lead extensions 16A and 16B are intended to be permanent. In contrast, the IPG 400 may be replaced when its power source fails or is no longer rechargeable. Advantageously, the IPG 400 can provide electrical stimulation to the patient through the plurality of electrode contacts.

As seen best in FIG. 2, the electrode assembly 80 typically interfaces with the IPG 400 via a set of lead extensions 16A and 16B or alternatively, electrode assembly 80' typically interfaces with the IPG 400 without requiring lead extensions. Electrode assemblies 80 or 80' may also be connected to an external trial stimulator (ETS) 300 through an OR cable 38 and connecting system 200. The external trial stimulator 300 includes the same pulse generation circuitry as does the IPG 400, and is used on a trial basis, e.g., for 7-10 days, after the electrode array system has been implanted, and prior to implantation of the IPG 400, in order to test the effectiveness of the stimulation that is to be provided.

Turning next to FIGS. 3A and 3B, a top view of stylet handle 22A and a cross sectional view of the stylet handle 22A are respectively shown. The cross-sectional view is taken along line 3B-3B shown in FIG. 3A. The proximal end 23A of stylet wire 15A may be permanently attached to the stylet handle 22A at location 25A as shown in FIG. 3B. Typical attachment methods known in the art may be used, e.g., adhesive bonding, attaching the stylet wire during the molding process of the stylet handle, or heat staking (which is a bonding method for joining metal parts to plastics parts). The stylet handle is typically made from a molded plastic material, or the like, in accordance with common practice in the art. The molded part of the stylet handle includes a front locking member 32A and a rear locking member 35A which are used to connect the stylet handle 22A to a connector platform 20 as explained in more detail below.

Figure 4A:
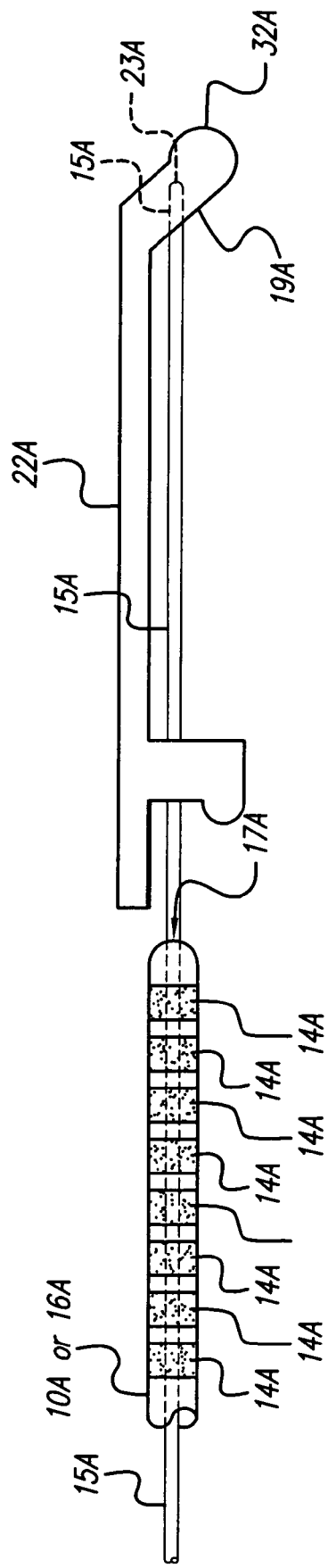
FIG. 4A is a side view of the stylet handle shown in FIG. 3A and further shows a stylet wire attached to the stylet handle being inserted through the central lumen of a lead or lead extension.

FIG. 4A shows the proximal end of the lead 10A or lead extension 16A (a lead extension 16A may or may not be required) being positioned within the stylet handle 22A. A stylet wire 15A is inserted through the lead's central lumen 17A until the proximal end of the lead is in contact with slanting edge 19A as seen best in FIG. 4B. It is to be emphasized that the stylet wire 15A is used to stiffen the lead during surgery, thus the stylet wire 15A runs through a central lumen along the entire length of the lead, including any required lead extensions. FIG. 4B shows a side view of the plurality of electrical terminals 14A positioned within the stylet handle 22A and FIG. 4C shows a bottom view of the lead extension 16A and stylet handle 22A positioned within the stylet handle 22A.

Figure 5A:
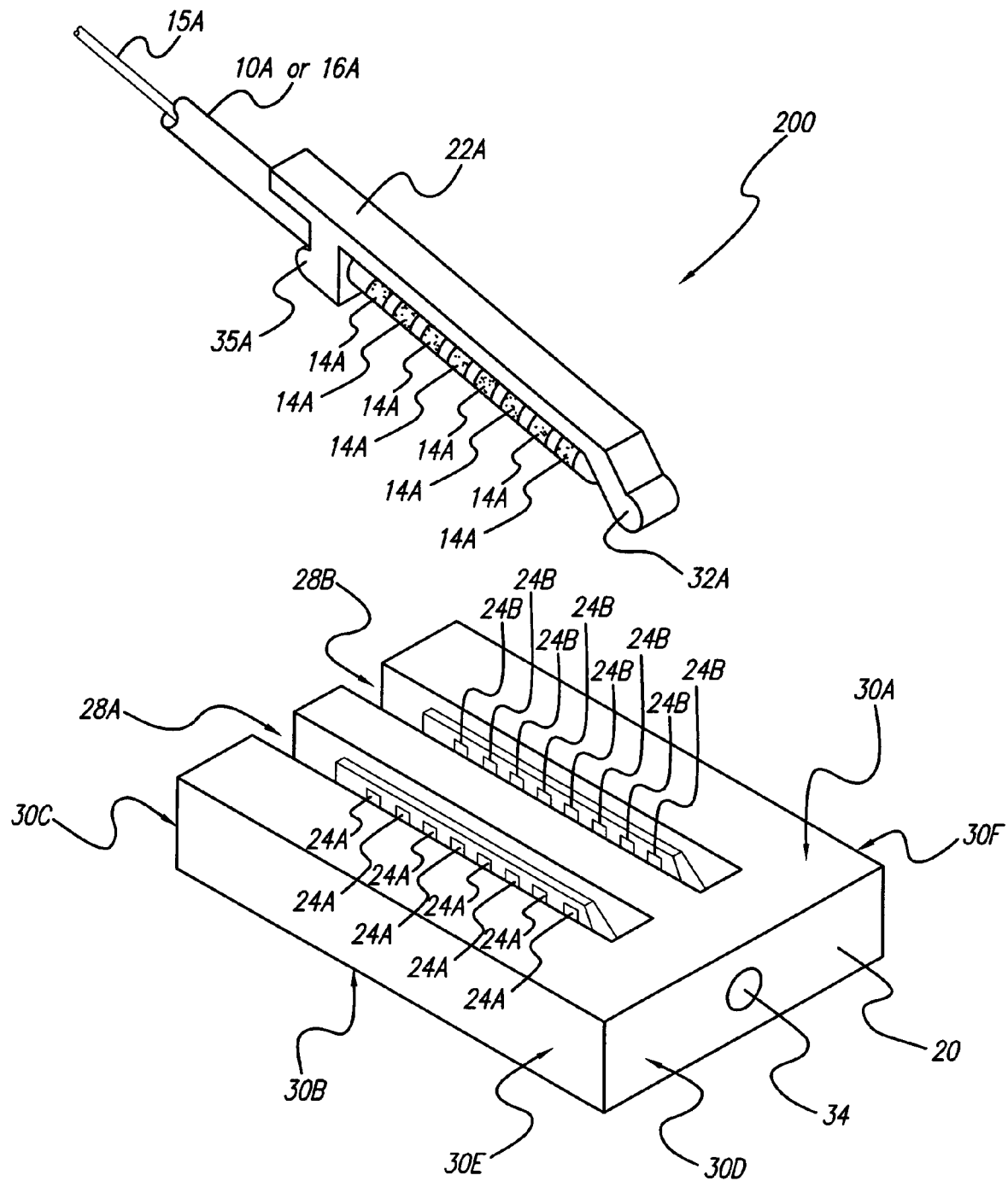
FIG. 5A is an exploded view of an exemplary embodiment of a connector system of the present invention.
Figure 5B:
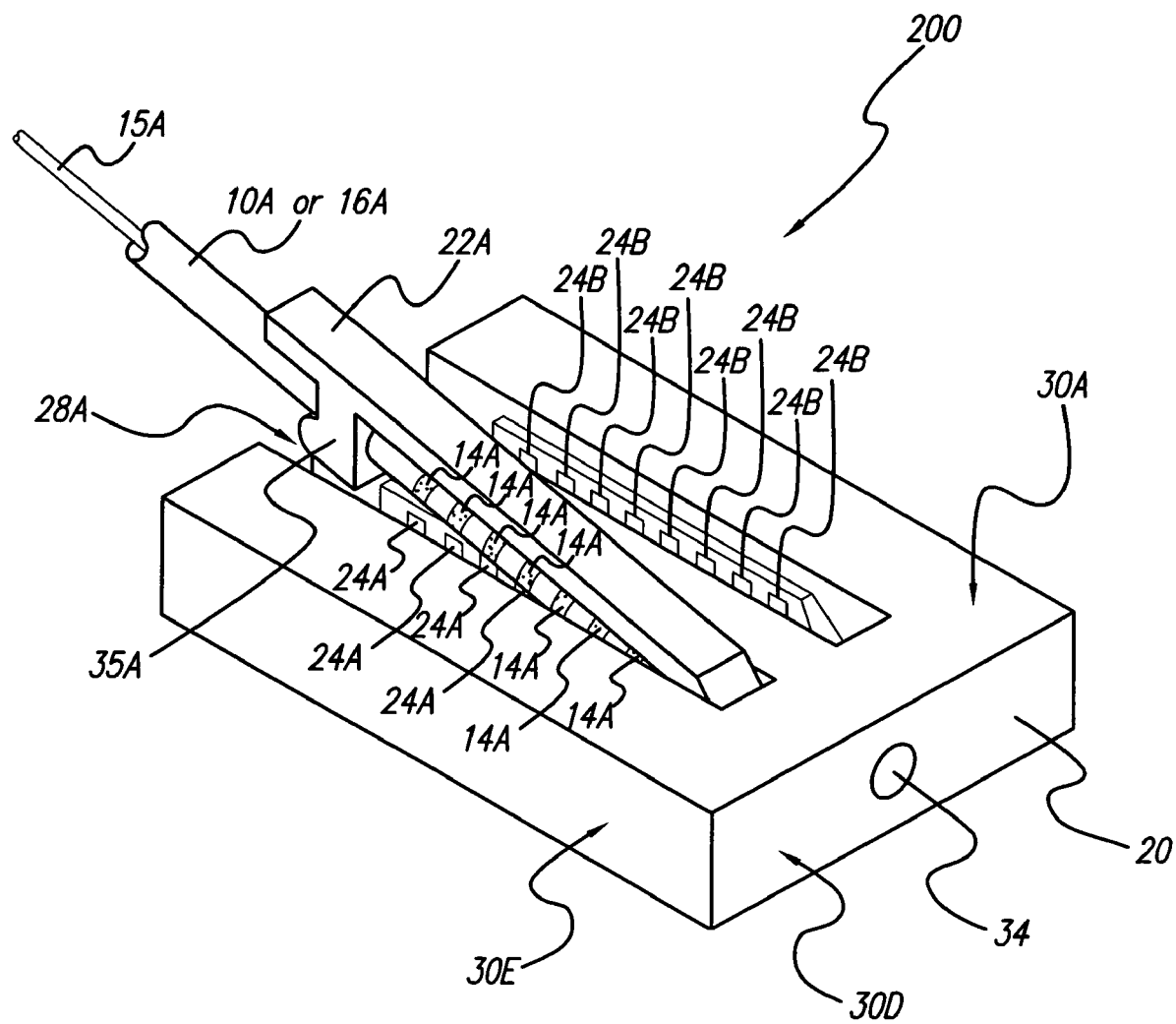
FIG. 5B is a perspective view of the connector system shown in FIG. 5A, with a stylet handle connected onto a first locking groove located within the connector platform of the present invention.

Turning next to FIG. 5A, an exemplary embodiment of a connector system 200 is shown that includes a connector platform 20 and a stylet handle 22A. The connector platform 20 may include a top surface 30A, an opposite bottom surface 30B, a rear surface 30C, an opposite front surface 30D, a left surface 30E, and an opposite right surface 30F. Within the connector platform 20, a plurality of spaced-apart mating contacts 24A and 24B are located within an attachment area or open slots 28A and 28B. The open slots 28A and 28B are shown being located on surface 30A, but may alternatively be located on any of the other surfaces 30B, 30C, 30D, 30E, or 30F. The attachment area within the connector platform 20 may also consists of closed slots or other suitable attachment means. The proximal end of the lead 10A or lead extension 16A is inserted into the stylet handle 22A and aligned to the connector platform 20 as shown in FIG. 5B. Mating contacts 24A align with the plurality of spaced-apart electrical terminals 14A, for simultaneous stimulation with a trial stimulator 300. The stylet handle 22A acts as a carrier for housing and protecting the proximal end of the lead 10A or lead extension 16A. The stylet handle 22A also acts as a quick connect interface that positively locates, locks, and unlocks into the connector platform 20. The connector platform 20 allows two stylet handles 22A and 22B to be engaged using open slots 28A and 28B respectively. Two exemplary open slots 28A and 28B are shown, but three or more could be made available. The additional open slots would allow the user the flexibility to have several engagement configurations available during the connection process of the ETS 300 or similar medical equipment.

In another aspect of the invention, open slots 28A and 28B are substantially parallel to each other and extend along surface 30A of the connector 20, disposing therein spaced-apart mating contacts 24A and 24B. The open slots 28A and 28B may also extend along any other surface of the connector 20. Stylet handle 22A is engaged along the longitudinal axis of slot 28A. The stylet handle 22A secures the proximal end of the lead 10A or lead extension 16A within open slot 28A. Likewise, the stylet handle 22B secures the proximal end of lead 10B or lead extension 16B using open slot 28B.

Figure 6:
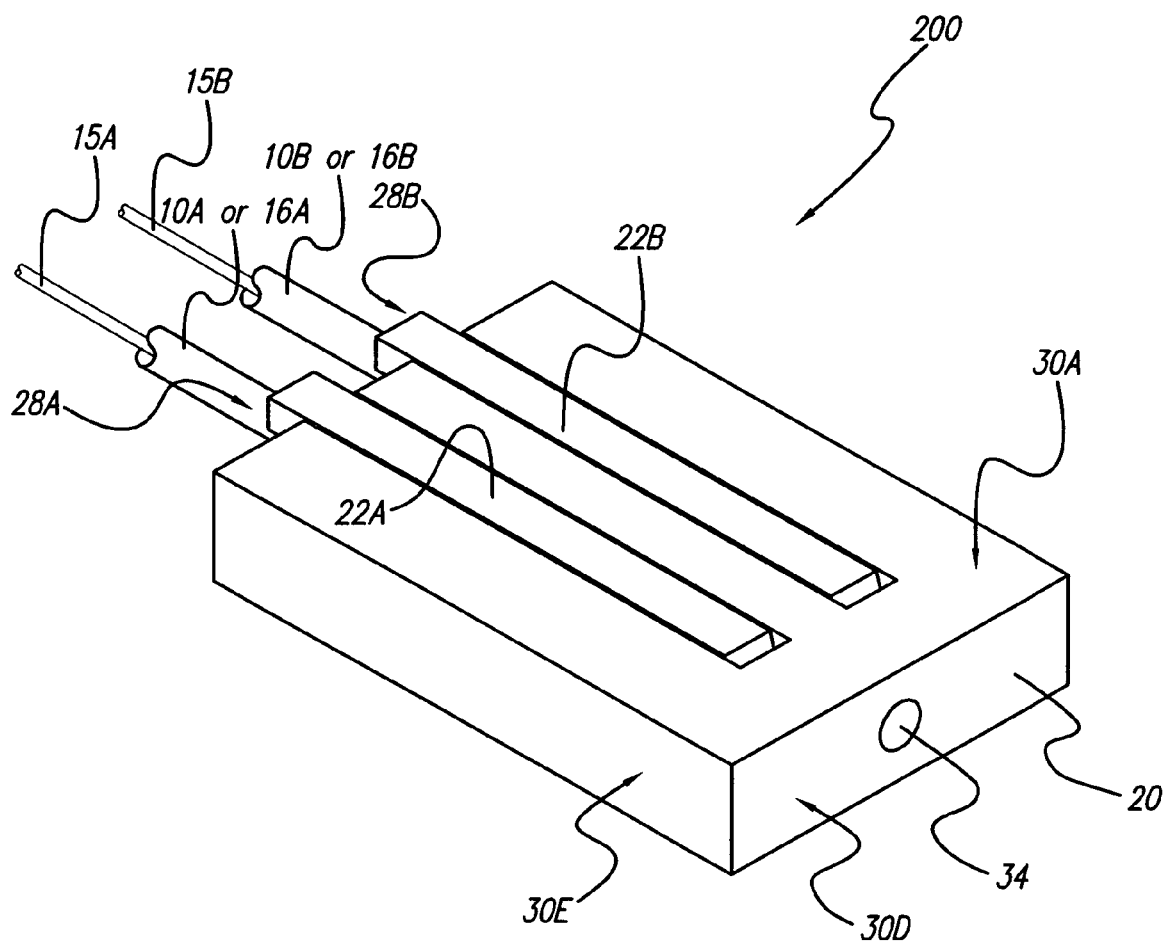
FIG. 6 is a perspective view of a connector system, with two stylet handles and two leads or lead extensions shown completely inserted within the attachment area of the connector system.

The connector platform 20 allows stylet handle 22A to house and protect spaced-apart electrical terminals 14A of the lead 10A or lead extension 16A. The stylet handle 22A further acts as a quick connect interface that positively locates and clips down onto open slot 28A of connector platform 20 as shown in FIG. 5B, where the front locking member 32A is initially secured onto open slot 28A. The stylet handle 22A is then locked in place when the rear locking member 35A snaps down onto open slot 28A. In a similar manner, the proximal end of lead 10B or lead extension 16B is likewise connected to connector platform 20 using stylet handle 22B and open slot 28B as shown in FIG. 6.

Figure 7A:
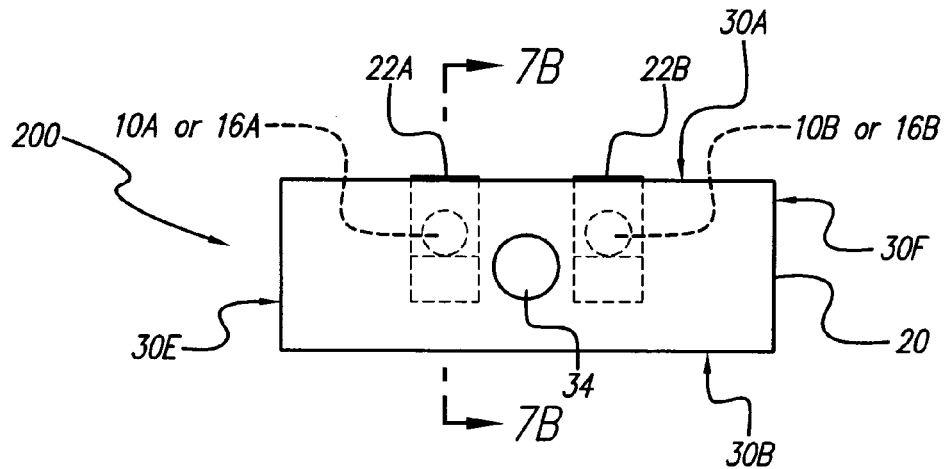
FIG. 7A is a front view of the connector system shown in FIG. 6.
Figure 7B:
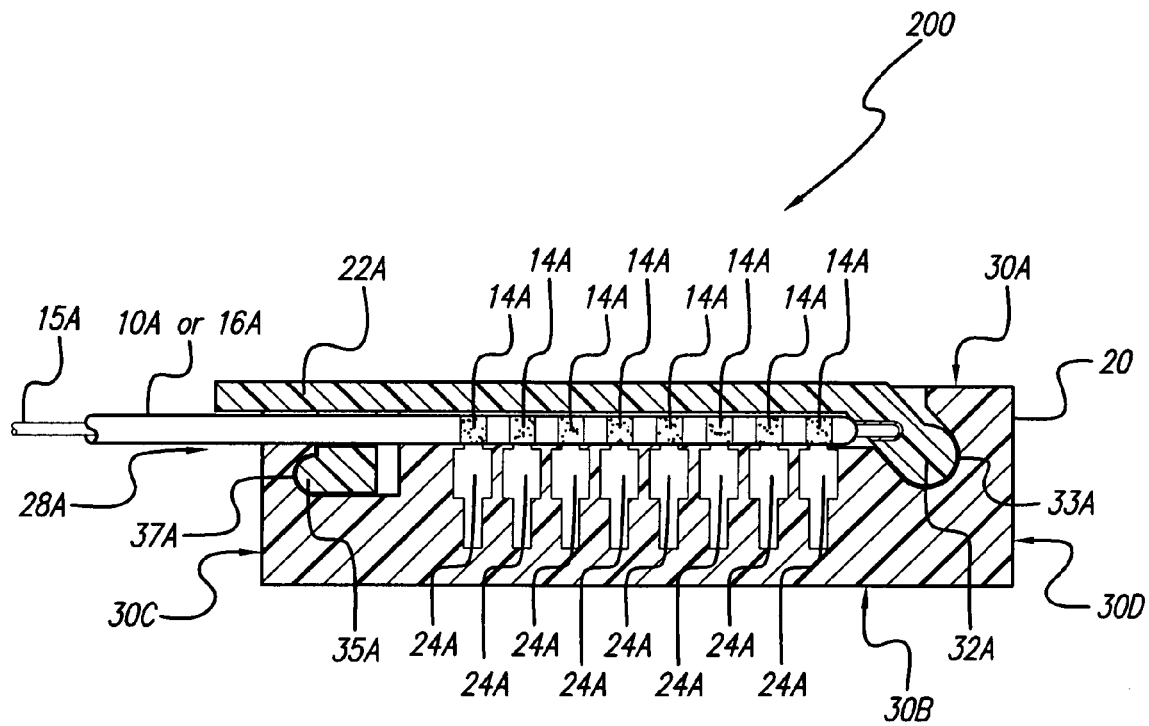
FIG. 7B is a cross sectional view of the connector system taken along sectional line 7B-7B shown in FIG. 7A.

FIG. 7A shows a front view of the connector platform 20. The lead 10A or lead extension 16A and stylet handle 22A are shown in their locked and aligned position in the cross sectional view FIG. 7B, taken along sectional line 7B-7B shown in FIG. 7A. The locking members 32A and 35A of the stylet handle 22A are positioned along the locking grooves 33A and 37A respectively. FIG. 7B shows a plurality of spaced-apart electrical terminals 14A positively aligned with a row of mating contacts 24A.

Open slots 28A and 28B can either be used to individually connect a stylet handle having a lead or lead extension housed therein, or the open slots 28A and 28B can be used as a pair, electrically connecting with another connector platform 20. Various connecting configurations can be obtained by having two or more parallel open slots available within the connector platform 20. The main advantage is to allow a multiple lead system 80 or 80' to be connected to an ETS 300.

Returning to FIG. 2, end 36A of the OR external cable 38, detachably connects to the ETS 300 through port 302A and end 36B connects to the ETS through port 302B. The end 36C of the OR external cable 38 detachably connects through opening 34 located on surface 30D of the connector platform 20. Opening 34 can alternatively be located on any other surface of the connector platform 20 depending on the orientation of the connecting slots. Alternatively, end 36C may be permanently wired to the connector platform 20.

The simple process of connecting a proximal end of an implantable lead to a stylet handle and then locking the stylet handle to a connector platform allows the user the advantage of minimizing the required steps in connecting the ETS 300 to the implanted SCS lead system. During the testing period, the ETS 300 can then be used to (1) optimize the position of the electrode arrays 12A and 12B along the dura of the spinal cord or other target tissue area; (2) test the efficacy of the electrode system, e.g., test the stimulation therapy for fitting purposes; and (3) provide valuable feedback through the use of a diagnostics module and patient interaction. After an optimal position for the electrode arrays 12A and 12B has been established, the stylet handles 22A and 22B may be disconnected from the connector platform 20 and the stylet wires 15A and 15B may be removed from the lead system. The lead system 80 or 80' may then be finally connected to an IPG 400, as shown in FIG. 1B.

Figure 8:
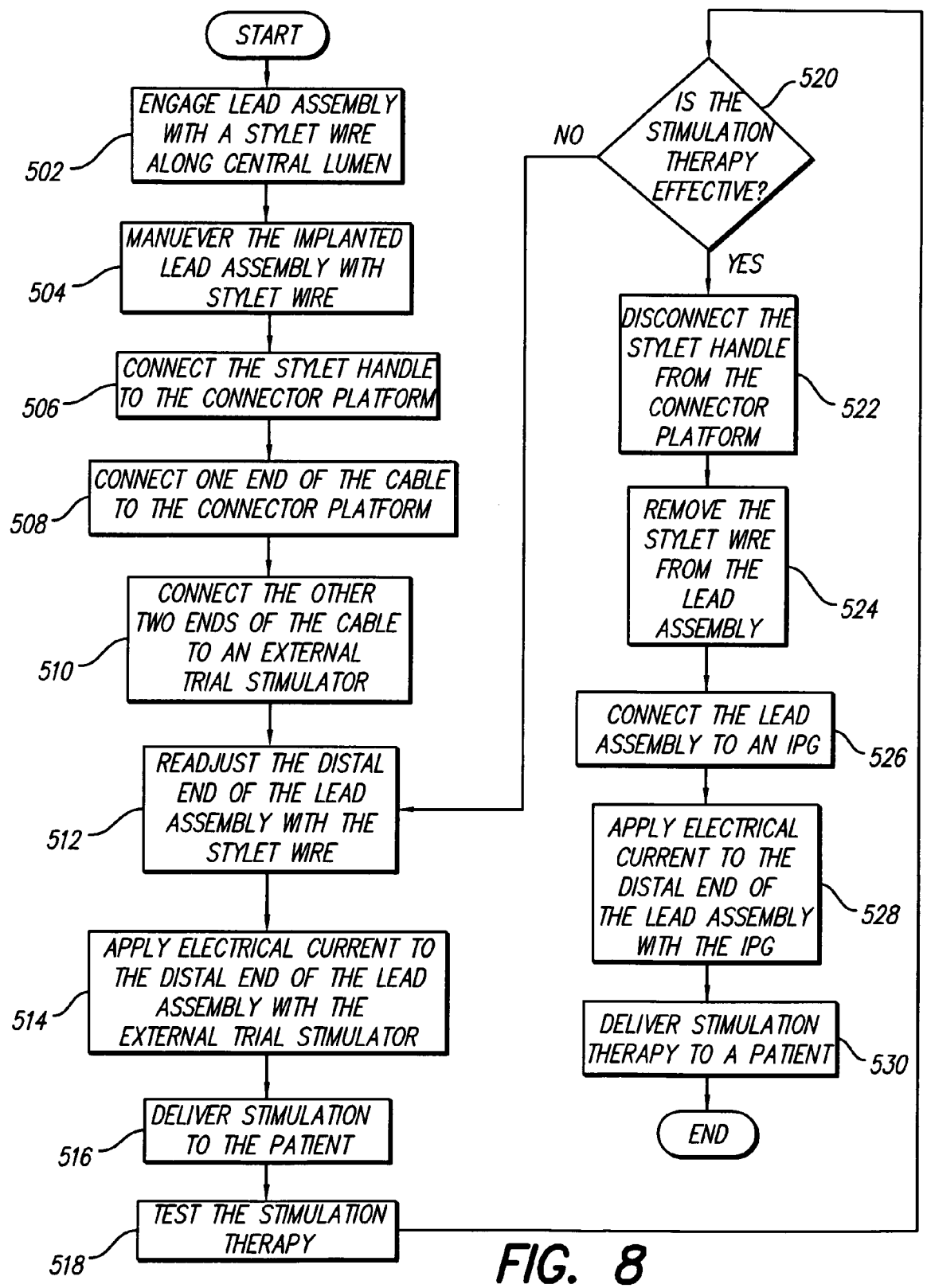
FIG. 8 is a flowchart depicting the steps used for positioning an electrode array along a dura space of a patient.

FIG. 8 shows a flowchart depicting exemplary steps for positioning an electrode array along a dura space (or other target tissue location) of a patient. The flowchart begins by engaging a respective stylet wire 15A or 15B to a lead assembly, 80 or 80' (block 502). It is to be emphasized that the lead assemblies 80 and 80' are only exemplary, two or more lead assemblies may be positioned. A stylet wire is typically threaded along a central lumen the entire length of the lead. The stylet wire stiffens the lead while the surgeon maneuvers the lead along the dura space (or other target tissue location) of the patient (block 504). Once a preliminary position of the electrode arrays 12A and 12B has been determined, each stylet handle 22A and 22B are connected to a connector platform 20 (block 506). A cable 38 is used to connect the connector platform 20 to the external trial stimulator 300 (blocks 508 and 510). As required, the distal end of each lead is readjusted with respective stylet wires 15A and 15B (block 512). Electrical current is applied to the distal end of the lead with the external trial stimulator 300 (block 514), thereby delivering stimulation current pulses to the patient (block 516). The efficacy of the electrode system is tested using, e.g., a diagnostics module and patient interaction (block 518). If the tested results are negative, the steps shown in blocks 512, 514, 516, and 518 are repeated until the stimulation therapy is shown to provide effective results (block 520). Once a satisfactory stimulation therapy has been determined, the stylet handles 22A and 22B are disconnected from the connector platform 20 (block 522), the respective stylet wires 15A and 15B are removed from the lead assembly (block 524), and the lead assembly is detachably connected to the IPG 400 (block 526). The IPG 400 is thereafter used for applying current stimulation pulses to the implanted electrode array (block 528). In this manner, effective stimulation therapy can thereafter commence through the use of the IPG 400 (block 530).

While the invention herein disclosed has been described by means of specific embodiments and applications thereof, numerous modifications and variations could be made thereto by those skilled in the art without departing from the scope of the invention set forth in the claims. For example, the embodiments discussed above are not limited to spinal cord stimulation systems and may be used with many kinds of stimulation systems such as, but not limited to, cochlear implants, cardiac stimulation systems, peripheral nerve stimulation systems, brain stimulation systems and microstimulators.

What is claimed is:

1. A connector for connecting at least one lead system to an external trial stimulator, the at least one lead system including a distal end and a proximal end, the distal end having a plurality of spaced-apart electrode contacts and the proximal end having a plurality of spaced-apart electrical terminals, the connector comprising:
   a connector platform having at least one open slot; and
   a stylet handle detachably connected to said connector platform inside the at least one open slot, wherein a stylet wire is permanently attached to said stylet handle, and wherein the stylet wire engages the at least one lead system through a central lumen.

2. The connector of claim 1 wherein the stylet wire is permanently attached to said stylet handle using an adhesive.

3. The connector of claim 1 wherein the stylet wire is permanently attached to said stylet handle using a heat staking process.

4. The connector of claim 1 wherein the connector platform has two or more open slots that extend along a surface of the connector platform.

5. The connector of claim 4 wherein the two or more open slots each include a plurality of spaced-apart mating contacts.

6. The connector of claim 5 wherein the plurality of spaced-apart mating contacts align with the plurality of spaced-apart electrical terminals.

7. A connector for connecting at least one lead system to an external trial stimulator, the at least one lead system including a distal end and a proximal end, the distal end having a plurality of spaced-apart electrode contacts and the proximal end having a plurality of spaced-apart electrical terminals, the connector comprising:
   a connector platform having at least one open slot; and
   a stylet handle detachably connected to said connector platform inside the at least one open slot, wherein a stylet wire is permanently attached to said stylet handle, wherein the stylet wire engages the at least one lead system through a central lumen, and wherein the stylet handle further comprises a carrier that encloses the proximal end of the at least one lead system.

8. The connector of claim 7 wherein the carrier comprises a front locking member that positively locates onto a front locking groove and a rear locking member that clips down onto a rear locking groove, both grooves dimensioned and positioned within the at least one open slot.

9. The connector of claim 8 wherein the at least one open slot comprises a plurality of mating contacts.

10. The connector of claim 9 wherein the plurality of mating contacts align with the plurality of spaced-apart electrical terminals.

11. A connector system for connecting at least one SCS lead assembly to an external trial stimulator, said at least one SCS lead assembly including a distal end and a proximal end, the distal end having a plurality of spaced-apart electrode contacts and the proximal end having a plurality of spaced-apart electrical terminals, the connector system comprising:
   a stylet handle, wherein a stylet wire is permanently attached to said stylet handle, and wherein said stylet wire engages the at least one SCS lead assembly through a central lumen; and
   attachment means for connecting the stylet handle to a connector platform such that a proximal end of the stylet handle does not extend beyond the connector platform.

12. The connector system of claim 11 wherein the attachment means comprises at least one open slot that extends along a surface of the connector platform, wherein the at least one open slot further comprises a plurality of mating contacts enclosed therein, and wherein the plurality of mating contacts align with the plurality of spaced-apart electrical terminals.

13. The connector system of claim 11 wherein the attachment means comprises two or more open slots that extend along a surface of the connector platform.

14. A connector system for connecting at least one SCS lead assembly to an external trial stimulator, said at least one SCS lead assembly including a distal end and a proximal end, the distal end having a plurality of spaced-apart electrode contacts and the proximal end having a plurality of spaced-apart electrical terminals, the connector system comprising:
   a stylet handle, wherein a stylet wire is permanently attached to said stylet handle, and wherein said stylet wire engages the at least one SCS lead assembly through a central lumen; and
   attachment means for connecting the stylet handle to a connector platform;
   wherein the attachment means comprises at least one open slot that extends along a surface of the connector platform, wherein the at least one open slot further comprises a plurality of mating contacts enclosed therein, wherein the plurality of mating contacts align with the plurality of spaced-apart electrical terminals, and wherein the stylet handle further comprises a carrier that encloses the proximal end of the at least one SCS lead assembly.

15. The connector system of claim 14 wherein the carrier further comprises a front locking member that positively locates onto a front locking groove and a rear locking member that clips down onto a rear locking groove, both grooves dimensioned and positioned within the at least one open slot.

16. A system for connecting at least one implantable lead to an external trial stimulator, the at least one implantable lead including a distal end and a proximal end, the distal end having a plurality of spaced-apart electrode contacts and the proximal end having a plurality of spaced-apart electrical terminals, the system comprising:
 a stylet handle having a stylet wire attached thereto, and wherein said stylet wire is adapted to engage the at least one implantable lead through a central lumen;
 a housing having at least one attachment area that extends along a surface of said housing, wherein the stylet handle is detachably connected to the at least one attachment area such that a proximal end of the stylet handle does not extend beyond the housing; and
 a cable having a first end connected to the housing, and a second end connected to the external trial stimulator.

17. The system of claim 16 wherein the housing further includes two or more attachment areas.

18. A system for connecting at least one implantable lead to an external trial stimulator, the at least one implantable lead including a distal end and a proximal end, the distal end having a plurality of spaced-apart electrode contacts and the proximal end having a plurality of spaced-apart electrical terminals, the system comprising:
 a stylet handle having a stylet wire attached thereto, wherein said stylet wire is adapted to engage the at least one implantable lead through a central lumen;
 a housing having at least one attachment area that extends along a surface of said housing, wherein the stylet handle is detachably connected to the at least one attachment area; and
 a cable having a first end connected to the housing, and a second end connected to the external trial stimulator;
 wherein the stylet handle further comprises a front locking member that positively locates onto a front locking groove and a rear locking member that clips down onto a rear locking groove, both grooves dimensioned and positioned within the at least one attachment area, wherein the at least one attachment area has a plurality of mating contacts associated therewith, and wherein the plurality of mating contacts align with the plurality of spaced-apart electrical terminals.

19. A connector for an electrical stimulation system, the connector comprising:
 a connector platform comprising a plurality of contacts disposed in at least one open slot defined in the connector platform; and
 a stylet configured and arranged for receiving a lead and coupling the lead with the connector platform, the stylet comprising
  a stylet wire having a first end and a second end, the first end configured and arranged for removable insertion into a central lumen defined in a proximal end of the lead, and
  a stylet handle attached to the second end of the stylet wire, wherein the stylet handle is configured and arranged for removably coupling with the at least one open slot in the connector platform such that a proximal end of the stylet handle does not extend beyond the connector platform, and also such that when the stylet wire is inserted into the central lumen defined in the proximal end of the lead, at least one terminal disposed on the proximal end of the lead aligns with at least one of the plurality of contacts disposed in the at least one open slot defined in the connector platform.

20. An electrical stimulation system comprising:
 a lead having a distal end and a proximal end, the lead comprising
  a central lumen extending from an opening in the proximal end,
  a plurality of electrodes disposed on the distal end of the lead,
  a plurality of terminals disposed on the proximal end of the lead, and
  a plurality of conductors, each conductor electrically coupling at least one of the electrodes to at least one of the terminals;
 a connector for an electrical stimulation system, the connector comprising
  a connector platform comprising a plurality of contacts disposed in at least one open slot defined in the connector platform; and
  a stylet configured and arranged for receiving a lead and coupling the lead with the connector platform, the stylet comprising
   a stylet wire having a first end and a second end, the first end configured and arranged for removable insertion into a central lumen defined in a proximal end of the lead, and
   a stylet handle attached to the second end of the stylet wire, wherein the stylet handle is configured and arranged for removably coupling with the at least one open slot in the connector platform such that a proximal end of the stylet handle does not extend beyond the connector platform, and also such that when the stylet wire is inserted into the central lumen defined in the proximal end of the lead, at least one terminal disposed on the proximal end of the lead aligns with at least one of the plurality of contacts disposed in the at least one open slot defined in the connector platform and
 an external trial stimulator electrically coupled to at least one of the plurality of contacts disposed in the at least one open slot defined in the connector platform.

* * * * *